United States Patent [19]

Chikama

[11] Patent Number: 4,718,760
[45] Date of Patent: Jan. 12, 1988

[54] APPARATUS FOR OPTICALLY INSPECTING OBJECT HAVING REFLECTING SURFACE

[75] Inventor: Toshio Chikama, Tokyo, Japan

[73] Assignee: Kabushiki Kaisha Machida Seisakusho, Tokyo, Japan

[21] Appl. No.: 765,670

[22] Filed: Aug. 14, 1985

[30] Foreign Application Priority Data

Aug. 18, 1984 [JP] Japan .................. 59-170997
Aug. 18, 1984 [JP] Japan ............. 59-125023[U]
Aug. 18, 1984 [JP] Japan ............. 59-125024[U]

[51] Int. Cl.⁴ ............................................. G01N 21/88
[52] U.S. Cl. ................................. 356/237; 356/241; 356/446
[58] Field of Search ............... 356/445, 446, 447, 448, 356/237, 241

[56] References Cited

U.S. PATENT DOCUMENTS

| | | | |
|---|---|---|---|
| 2,471,750 | 5/1949 | Hunter | 356/448 |
| 4,326,808 | 4/1982 | Pryor et al. | 356/445 |
| 4,629,319 | 12/1986 | Clarke et al. | 356/237 |

FOREIGN PATENT DOCUMENTS

| | | | |
|---|---|---|---|
| 2820910 | 11/1978 | Fed. Rep. of Germany | 356/445 |
| 1288199 | 9/1972 | United Kingdom | 356/241 |

*Primary Examiner*—F. L. Evans
*Attorney, Agent, or Firm*—Kane, Dalsimer, Kane, Sullivan & Kurucz

[57] ABSTRACT

Apparatus for optically inspecting an object having a reflecting surface includes an irradiating device for emitting illuminating light; a shield member for reflecting the illuminating light to irradiate the object, and a light-receiving device for receiving an image of the object irradiated through the reflection of the illuminating light by the shield member. The shield member covers an extent of a field of vision of the light-receiving device through the reflection of the reflecting surface.

4 Claims, 19 Drawing Figures

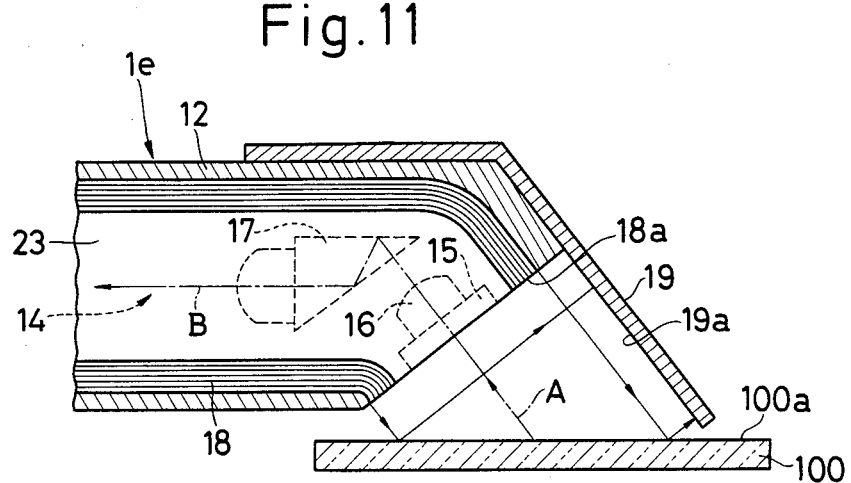
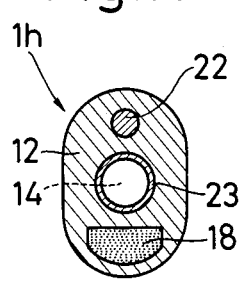
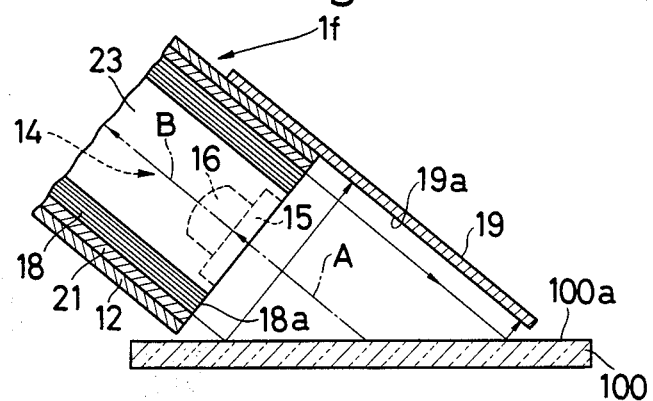
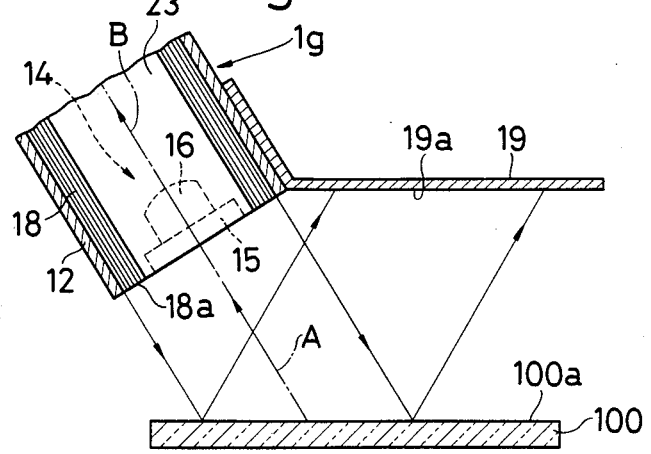

APPARATUS FOR OPTICALLY INSPECTING OBJECT HAVING REFLECTING SURFACE

BACKGROUND OF THE INVENTION

1. Field of the Invention

This invention relates to apparatus for optically inspecting an object having a reflecting surface to determine whether the object has any defect such as a flaw, stain and dirt.

2. Prior Art

Examples of objects to be optically inspected include a sheet 100 (FIG. 4), such as a polished metal sheet, having a front surface 100a serving as a mirror surface or reflecting surface, a transparent sheet 100 (FIG. 5) having a front surface 100a serving as a reflecting surface, and a multi-layer structure 100 (FIG. 6) composed of a plurality of layers, all of the layers being transparent except for the lowermost layer, and the uppermost layer having a front surface 100a serving as a reflecting surface. One example of the multi-layer structure is a semi-conductor board having a plurality of transparent coating layers thereon.

The sheet 100 of FIG. 4 is inspected to determine whether there is any defect a such as as flaw, stain or dirt on the reflecting surface 100a. The sheet 100 of FIG. 5 is inspected to determine whether there are any defects b on the reflecting surface 100a and the rear surface and in the interior. The multi-layer structure 100 of FIG. 6 is inspected to determine whether there are any defects c on the reflecting surface 100a and at the boundary between the layers and any separation d at the boundary between the layers.

FIG. 7 shows a conventional device for optically inspecting the objects 100 which device comprises a probe 110 having a light-receiving portion 111 at its front end, an irradiating means 112 in the form of an electric-light bulb placed in spaced relation to the probe 110, and a concave mirror 113 to which the irradiation means 112 is secured. Rays of light emitted from the irradiation means 112 are reflected by the concave mirror 113 and are directed toward an object 100 to be inspected, so that these rays of light are reflected by a reflecting surface 100a of the object 100 and are fed to the light-receiving portion 111 of the probe 110. Thus, the object 100 is illuminated with high brightness to enable any defect (for example, those defects indicated above by a, b, c and d) to be detected. However, this conventional device is relatively expensive since the irradiation means 112 and the light-receiving portion 111 are separate. In addition, time and labor are required for properly orienting the irradiation means 112 and the light-receiving portion 111. Further, this conventional device is rather space-consuming.

To overcome this difficulty, it has been proposed to provide a probe 120 (FIG. 8) which is similar in construction to a conventional endoscope and has a light-receiving portion 121 and an irradiating portion 122 at its front end. The front end of the probe 120 is disposed in opposed relation to the front surface 100a of the object 100 to irradiate it to carry out the inspection. With this probe however, an image of the irradiating portion 122 is reflected by the reflecting surface 100a of the object 100 and is fed to the light-receiving portion 121, thereby causing halation. This adversely affects the S-N ratio when processing an image signal obtained, and therefore an image of a defect present in the object can not be accurately detected.

It may be considered to dispose the probe 120 obliquely with respect to the object 100 to irradiate illuminating light to the reflecting surface 100a at an angle so as to prevent an image of the irradiating portion 122 from being fed to the light-receiving portion 121. In this case, however, the illuminating light is reflected by the reflecting surface 100a to irradiate the background, so that an image of the background is reflected by the reflecting surface 100a and is fed to the light-receiving portion 121. Therefore, in this case, the S-N ratio is also affected as described above, and an image of a defect present in the object can not be accurately detected.

SUMMARY OF THE INVENTION

It is therefore an object of this invention to provide apparatus for optically inspecting an object which is relatively inexpensive, space-saving and can accurately detect a defect on the object easily.

According to the present invention, there is provided apparatus for optically inspecting an object having a reflecting surface which comprises irradiating means for emitting illuminating light; shield means for reflecting the illuminating light to irradiate the object, and light-receiving means for receiving an image of the object irradiated through the reflection of the illuminating light by the shield means, the shield means covering an extent of a field of vision of the light-receiving means through the reflection of the reflecting surface.

BRIEF DESCRIPTION OF THE DRAWINGS

FIGS. 9 to 13 are cross-sectional views of further modified probes;

FIG. 14 is a cross-sectional view of a further modified probe;

DESCRIPTION OF THE PREFERRED EMBODIMENTS OF THE INVENTION

Figure 1:
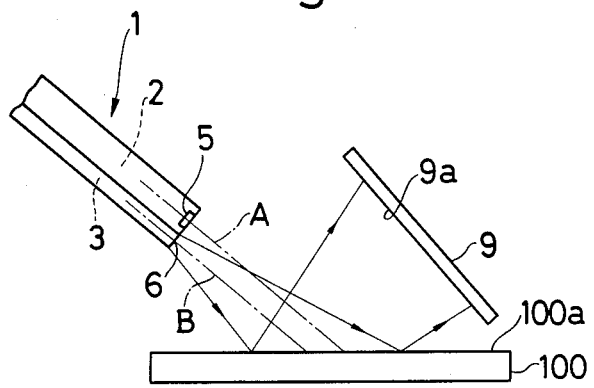
FIG. 1 is a side-elevational view of a probe provided in accordance with the present invention.

The invention will now be described with reference to the accompanying drawings in which like reference numerals denote corresponding parts in several view.

A probe 1 shown in FIG. 1 is similar in construction to a rigid insertion portion of a conventional endoscope and includes an elongated hollow body. The probe 1 comprises an image-transmitting optical system 2 mounted in the body and a bundle 3 of optical fibers mounted in and extending along the body. The optical system 2 includes a light-receiving portion 5 and an objective lens both of which are disposed at the front end of the probe body. The optical system 2 further includes an ocular lens (not shown) disposed at the rear end of the probe body and a plurality of lenses interposed between the objective lens and the ocular lens. The front end of the optical fiber bundle 3 disposed at the front end of the probe body open to serve as an irradiating portion 6, the irradiating portion 6 being disposed in the vicinity of the light-receiving portion 5. The optical axis A of the optical system 2 is substantially parallel to the axis of the optical fiber bundle 3.

The rear end of the optical fiber bundle 3 is connected to a light source so that light fed from the light source can emit from the irradiating portion 6. The inspection is carried out through the ocular lens with the eye. Alternatively, the image through the ocular lens is taken by either a camera or television camera.

Reference numeral 9 designates a shield plate having a surface 9a which is a diffusion surface of a white color causing the diffused reflection of light, the surface 9a having no pattern on it.

Figure 4:
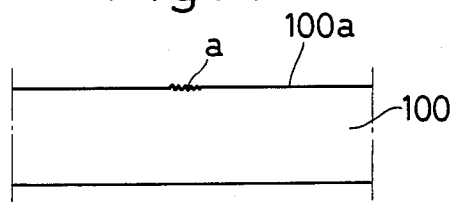
FIGS. 4 to 6 are views of objects to be inspected.
Figure 5:
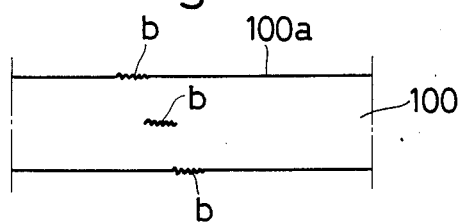
Figure 6:
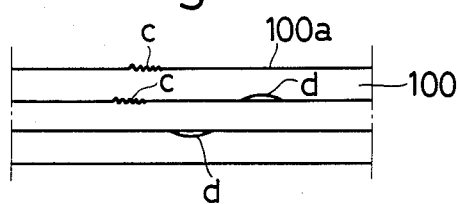
Figure 8:
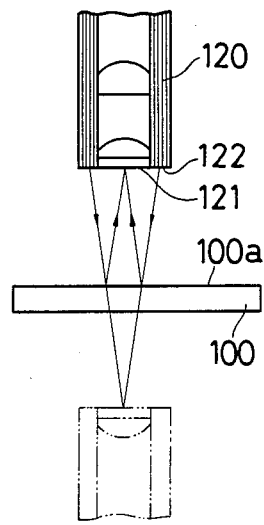
FIGS. 7 and 8 are cross-sectional views of conventional inspecting devices.
Figure 7:
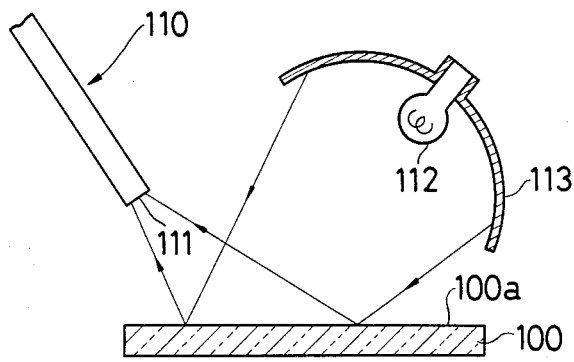

The probe 1 can inspect any of the objects 100 shown in FIGS. 4 to 6.

First, the probe 1 is disposed obliquely with respect to an object 100 in the form of a sheet to be inspected. The shield plate 9 is also inclined with respect to the object 100 and is disposed in mirror image relation to the front end of the probe 1 with respect to the surface 100a of the object 100. In other words, the shield plate 9 is disposed in such a position that it covers an extent of irradiation of the irradiating portion 6 through the reflection of the surface 100a and an extent of a field of vision of the light-receiving portion 5 through the reflection of the surface 100a.

With this arrangement, illuminating light is applied from the irradiating portion 6 to the object 100, the direction of rays of illuminating light being oblique with respect to the surface 100a of the object. The rays of light are reflected by the surface 100a and directed to the shield plate 9 by which the rays of light are subjected to diffused reflection to irradiate the object 100 brightly. The image of the object 100 thus irradiated is transmitted via the optical system 2 and is taken by a television camera or the like. At this time, the object is brightly irradiated uniformly, and therefore not only a defect on the surface 100a but also defects in the interior and on the rear surface can be accurately detected. Where the defect is a separation d (see FIG. 6), it can be detected as an iris.

The direction of irradiation is oblique with respect to the surface 100a of the object 100, so that the image of the irradiation portion 6 of great brightness is reflected toward the shield plate 9 by which it is subjected to diffused reflection and hence is not fed to the light-receiving portion 5. Therefore, the S-N ratio is not affected when processing the image signal or data, and any defect present in the object can be accurately detected.

Further, the illuminating light is reflected by the surface 100a of the object 100 and is intercepted by the shield plate 9, so that it will not irradiate the background. In addition, an image of the background is intercepted by the shield plate 9 and therefore will not be fed to the light-receiving portion 5 via the surface 100a of the object 100. In this respect, also, S-N ratio is not affected.

Figure 2:
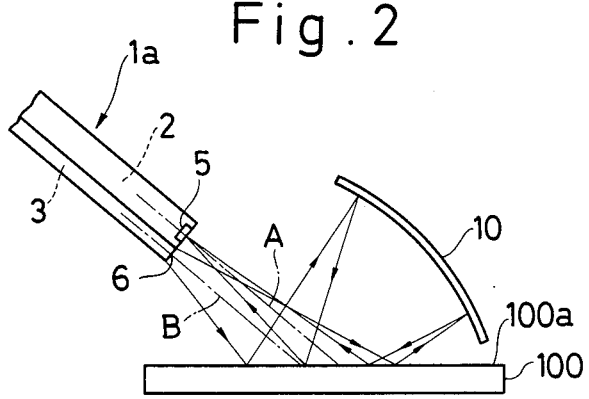
FIG. 2 is a view similar to FIG. 1 but showing another modified probe.

FIG. 2 shows a modified probe 1a which differs from the probe 1 of FIG. 1 in that a shield plate 10 is made of a concave mirror. In this embodiment, illuminating light from the irradiating portion 6 is reflected by the shield plate 10 back to the surface 100a of the object 100 and is further reflected by the surface 100a to be fed to the light-receiving portion 5. The concave mirror 10 is so positioned that its focus is disposed at the light-receiving portion 5. The focus may be disposed near the light-receiving portion 5. Since the image of the irradiating portion 6 is reflected by the concave mirror 10, it is not fed to the light-receiving portion 5 as an appreciable image. Therefore, the irradiating portion 6 will not affect the inspection of a defect in the object 100. The probe 1a in this embodiment can irradiate the object 100 with greater brightness than the probe 1 of FIG. 1, and therefore is well suited for detecting a defect in the interior of the object and a defect on the rear surface thereof.

The shield plates 9 and 10 may have a light-absorbing surface of a black color so that the rays of light applied thereto can be suitably absorbed thereinto without being reflected by it, in which case a defect on the reflecting surface 100a of the object 100 can only be detected.

Figure 3:
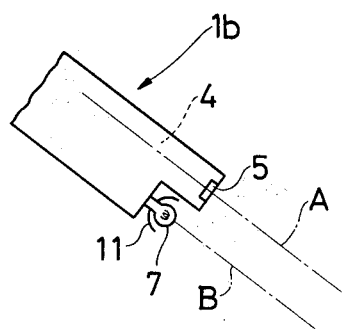
FIG. 3 is a fragmentary side-elevational view of a further modified probe.

Although the irradiating portion is formed by the front end of the optical fiber bundle in the above embodiments, the irradiating portion may be formed by an electric-light bulb 7 having a concave mirror 11 and secured to the front end of a probe 1b as shown in FIG. 3, in which case an optical axis B of the illuminating light emitted from the bulb 7 is substantially parallel to the optical axis A of an image-transmitting optical system 4.

Figure 9:
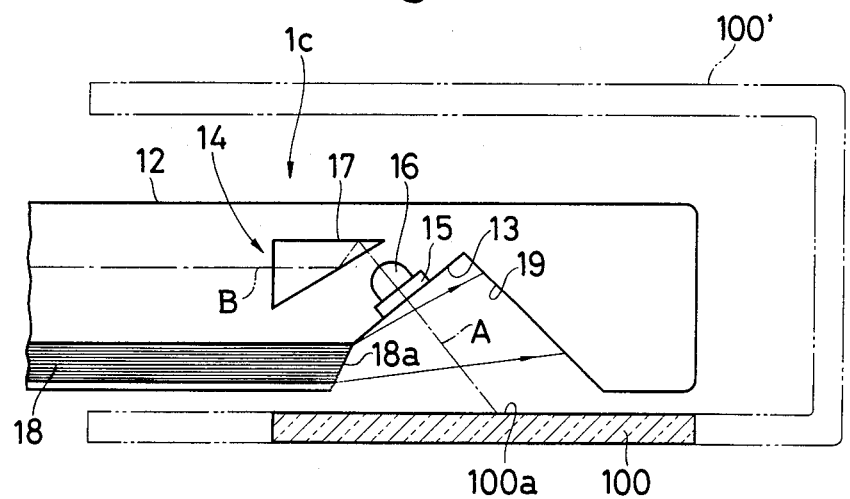

FIG. 9 shows a further modified probe 1c similar in construction to a rigid insertion portion of a conventional endoscope, the probe 1c comprising a tubular body 12 having a generally inverted V-shaped notch 13 formed in its lower portion adjacent to its front end, the notch 13 being defined by front and rear surfaces. An image-transmitting optical system 14 is mounted in the body 12, and a bundle 18 of optical fibers is mounted in and extends along the body 12. The optical system 14 comprises a light-receiving window or portion 15 attached to the rear edges of the notch 13 remote from the front end of the body 12, an objective lens 16 mounted on the light-receiving window 15, a prism 17 disposed adjacent to the objective lens 16, and an ocular lens (not shown) disposed at the rear end of the body 12. The optical system 14 further includes a plurality of lenses interposed between the objective lens 16 and the ocular lens. A common optical axis A of the light-receiving window 15 and objective lens 16 disposed obliquely with respect to an optical axis B of that portion of the optical system 14 extending between the ocular lens and the prism 17 and is directed downwardly. The optical axes B and A are interconnected via the prism 17.

The front end of the optical fiber bundle 18 opens to the rear edges of the notch 13 to provide an irradiating portion 18a, the irradiating portion 18a being disposed adjacent to the light-receiving portion 15. The front end of the optical fiber bundle 18 is cut obliquely and ground so that illuminating light emitted from the irradiating portion 18a can be directed obliquely upwardly as indicated by arrows in FIG. 9. The rear end of the optical fiber bundle 18 is connected to a light source.

The front surface 19 of the notch 13 serves as a flat reflecting surface and is disposed in obliquely opposed relation to the irradiating portion 18a. The reflecting surface 19 is a diffusion surface of a white color causing the diffused reflection of light.

In operation, the probe body 12 is first disposed substantially parallel to an object 100 to be inspected. The illustrated object 100 is in the form of a sheet, but it may be of a tubular form as indicated at 100' in dots and dash lines in FIG. 9. Then, the irradiating portion 18a irradiates illuminating light. This illuminating light is not directly fed to the object 100 but is reflected by the reflecting surface 19 and is subjected to diffused reflection. As a result, the object 100 is irradiated brightly by indirect illumination. The image of the object 100 thus irradiated is transmitted via the light-receiving portion 15 and the optical system 14 and is taken by a television camera or the like. At this time, the object 100 is brightly irradiated uniformly, and therefore not only a defect on the front surface 100a of the object 100 but also defects in the interior and on the rear surface can be accurately detected. Where the defect is a separation d (see FIG. 6), it can be detected as an iris.

The image of the irradiation portion 18a of great brightness is subjected to diffused reflection by the reflecting surface 19 and hence is not fed to the light-receiving portion 15. Therefore, the S-N ratio is not affected when processing the image signal or data, and any defect present in the object can be accurately detected.

Further, the illuminating light is intercepted by the reflecting surface 19 and therefore will not irradiate the background, so that an image of the background will not be fed to the light-receiving portion 15 via the surface 100a of the object 100. In this respect, also, the S-N ratio is not affected. The reflecting surface 19 is disposed in such a position that it covers an extent of irradiation of the irradiating portion 18a and an extent of a field of vision of the light-receiving portion 15 achieved by the reflection of the surface 100a.

Figure 10:
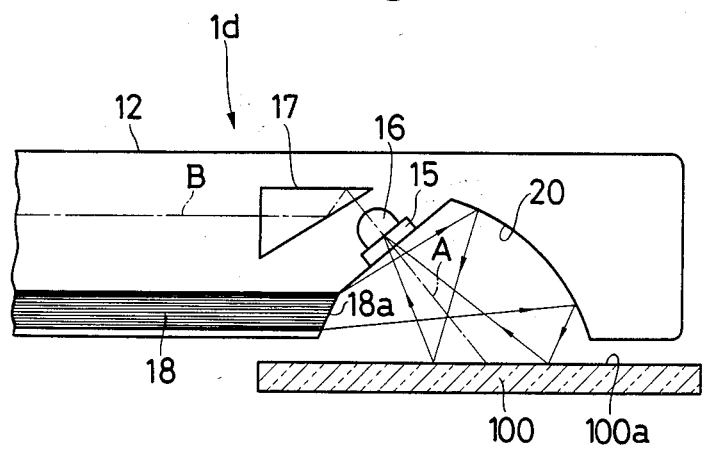

FIG. 10 shows a further modified probe 1d which differs from the probe 1c of FIG. 9 in that a reflection surface 20 is formed by a concave mirror. In this embodiment, illuminating light emitted from the irradiating portion 18a is reflected by the reflecting surface 20 and fed to the surface 100a of the object 100 by which the illuminating light is reflected toward the light-receiving portion 15. The focus of the reflecting surface 20 is disposed at the objective lens 16. The focus may be disposed near the objective lens 16. The image of the irradiating portion 18a is reflected by the reflecting surface 20 in the form of a concave mirror, and therefore is not fed to the light-receiving portion 15 as an appreciable image. The probe 1d in this embodiment can irradiate the object 100 with great brightness, and therefore is well suited for detecting a defect in the interior of the object and a defect on the rear surface thereof.

FIG. 11 shows a further modified probe 1e which differs from the probe 1c of FIG. 9 mainly in that a cross-sectionally circular bundle 18 of optical fibers is mounted within a tubular body 12 and extends therealong and in that a shield plate 19 is secured to the outer surface of the tubular body 12 at a front end thereof. The front end of the tubular body 12 is slightly bent downwardly and is cut obliquely, and the optical fiber bundle 18 fitted on the inner surface of the tubular body 12 is also bent downwardly at its front end. An inner tube 23 is received within the optical fiber bundle 18 of a circular cross-section, and the image-transmitting optical system 14 is mounted within the inner tube 23.

The shield plate 19 is of a generally V-shape and has a front half disposed substantially parallel to the common optical axis A of the light-receiving window 15 and objective lens 16, the front half of the shield plate 19 having an inner flat surface 19a which is a diffusion surface of a white color causing the diffused reflection of light.

In operation, the probe body 12 is first disposed substantially parallel to an object 100 to be inspected. Then, the irradiating portion 18a feeds illuminating light to the object 100, the direction of feed of the illuminating light being inclined with respect to the surface 100a of the object 100. The illuminating light is reflected by the surface 100a and is fed to the surface 19a of the shield plate 19 by which the illuminating light is diffusedly reflected to irradiate the object 100 brightly. An image of the object 100 thus irradiated is fed via the light-receiving portion 15 and the optical system 14 to the ocular lens at the rear end of the tubular body and is taken by a television camera or the like. At this time, the object 100 is brightly irradiated uniformly, and therefore not only a defect on the surface 100a but also defects in the interior and on the rear surface can be accurately detected. Where the defect is a separation d (see FIG. 6), it can be detected as an iris.

The direction of irradiation is oblique with respect to the surface 100a of the object 100, so that the image of the irradiation portion 18a of great brightness is reflected toward the shield plate 19 by which it is subjected to diffused reflection and hence is not fed to the light-receiving portion 15. Therefore, the S-N ratio is not affected when processing the image signal or data, and any defect present in the object can be accurately detected.

Further, the illuminating light is reflected by the surface 100a of the object 100 and is intercepted by the shield plate 19, so that it will not irradiate the background. In addition, an image of the background is intercepted by the shield plate 19 and therefore will not be fed to the light-receiving portion 15 via the surface 100a of the object 100. In this respect, also, the S-N ratio is not affected. Thus, the shield plate 19 covers an extent of irradiation of the irradiating portion 18a by the reflection of the surface 100a and an extent of a field of vision of the light-receiving portion 15 achieved by the reflection of the surface 100a.

FIG. 12 is a further modified probe 1f which differs from the probe 1e of FIG. 11 in that a tubular body 12 is straight with the optical axis A aligned with the optical axis B and in that a shield plate 19 is secured to the outer surface of the body 12 in parallel relation to the axis of the body 12. An optical fiber bundle 18 is also straight, and an auxiliary tube 21 is interposed between the body 12 and the optical fiber bundle 18, and the tubular body 12 is rotatable relative to the auxiliary tube 21 and movable therealong. With this construction, the position of the shield plate 19 is suitably adjusted to achieve the optimum irradiation effect. In operation, the probe body 12 is disposed obliquely with respect to the object 100, so that the direction of feed of the illuminating light from the irradiating portion 18a is also oblique relative to the surface 100a of the object 100.

FIG. 13 shows a further modified probe 1g which differs from the probe 1f of FIG. 12 in that the auxiliary tube 21 is omitted and in that a shield plate 19 is secured to the outer surface of the tubular body 12 in oblique relation to the axis of the body 12. In operation, the probe body 12 is disposed obliquely with respect to the object 100, and the shield plate 19 disposed parallel to the object 100. If the shield plate 19 is long, the inspection can also be carried out with the probe 1g disposed remote from the object 100.

FIG. 14 shows a further modified probe 1h in which a bundle 18 of optical fibers and an image-transmitting optical system 14 are mounted within a body 12 in non-coaxial relation. A shaft 22 mounted in the body 12 so as to be rotatable relative thereto and movable along an axis thereof, a front end of the shaft 22 extending beyond the front end of the body. A shield plate (not shown) is secured to the front end of the shaft 22. With this construction, the position of the shield plate can be adjusted.

Figure 15:
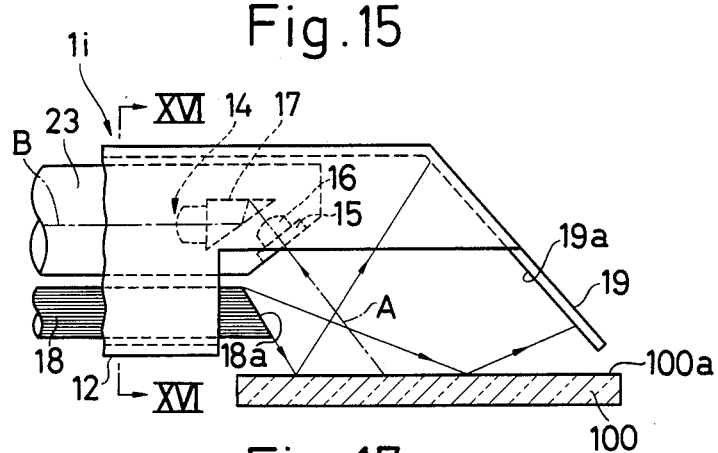
FIG. 15 is a cross-sectional view of a further modified probe.
Figure 16:
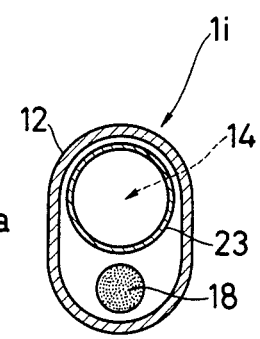
FIG. 16 is a cross-sectional view taken along the line XVI—XVI of FIG. 15.

FIGS. 15 and 16 show a further modified probe 1i in which an image-transmitting optical system 14 and a bundle 18 of optical fibers are mounted within a tubular body 12 in non-coaxial relation. A tubular body 12 is open at its front end and has an integral shield plate 19 formed at its front end and slanting downwardly in a direction away from a light-receiving portion 15. A front end of an optical fiber bundle 18 serving as an irradiating portion 18a is cut obliquely and faces the shield plate 19, so that illuminating light from the irradiating portion 18a is directed obliquely downwardly toward an object 100 as shown in FIG. 15. A common axis of a light-receiving portion 15 and objective lens 16 is also disposed obliquely with respect to the object 100.

Figure 17:
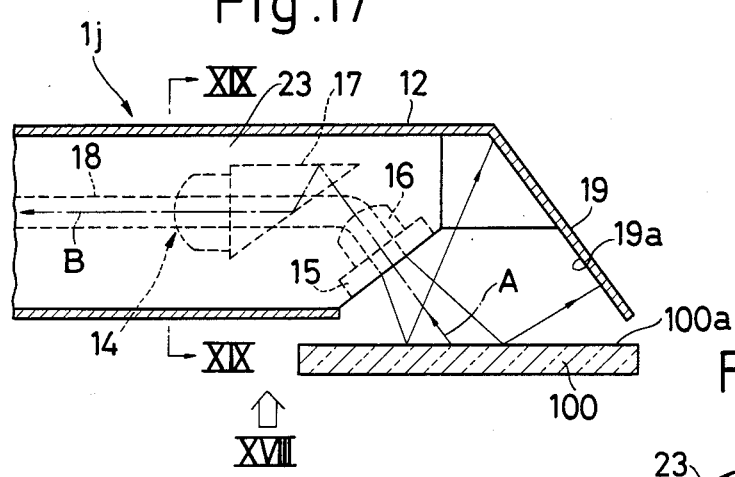
FIG. 17 is a cross-sectional view of a further modified probe.
Figure 19:
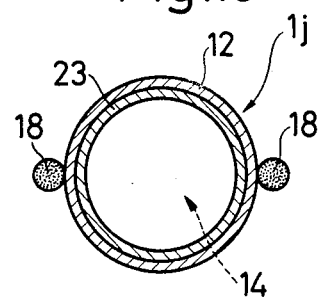
FIG. 19 is a cross-sectional view taken along the line XIX—XIX of FIG. 17.
Figure 18:
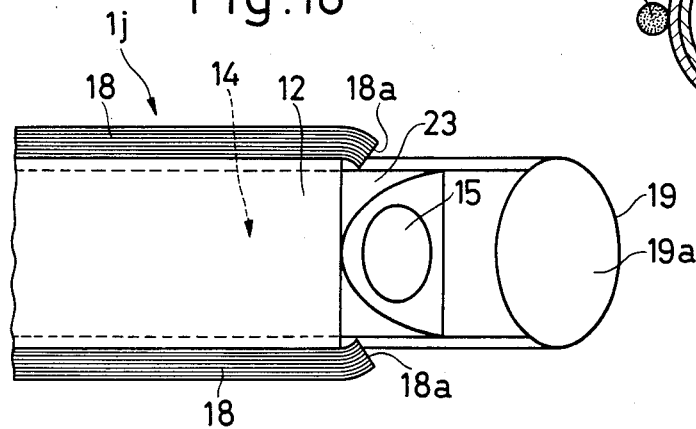
FIG. 18 is a view as seen in a direction XVIII of FIG. 17.

FIGS. 17 to 19 show a further modified probe 1j in which a pair of optical fiber bundles 18 are secured to the outer surface of a tubular body 12 in diametrically opposed relation. An inner tube 23 is received in the tubular body 12, and an image-transmitting optical system 14 is received in the inner tube 23. The tubular body 12 is open at its front end and has an integral shield plate 19 formed at its front end and slanting downwardly in a direction away from a light-receiving portion 15. The tubular body 12 is rotatable relative to the inner tube 23 and is movable therealong so that the position of the shield plate 19 can be adjusted. A common axis of a light-receiving portion 15 and objective lens 16 is also disposed obliquely with respect to the object 100. The front ends of the optical fiber bundles 18 are oriented inwardly and downwardly, and illuminating light from each of irradiating portions 18a is fed to an object 100 in the vicinity of a point where the axis A intersects the object 100.

While the probes according to the invention have been specifically shown and described herein, the invention itself is not to be restricted by the exact showing of the drawings or the description thereof. For example, in the above embodiments, although the light-receiving portion and the image-transmitting optical system are similar in construction to an insertion portion of a conventional endoscope, they may be replaced by a photosensor and an image sensor.

What is claimed is:

1. An apparatus for optically inspecting defects on and/or within an object having a reflecting surface comprising:
   (a) irradiating means for emitting illuminating light;
   (b) shield means having a reflecting surface for reflecting the illuminating light to irradiate the object, and
   (c) an image-transmitting optical system including light-receiving means for receiving an image of the object irradiated through the reflection of the illuminating light by said shield means, and means for optically transmitting the image of the object received by said light-receiving means, and said shield means covering an extent of a field of vision of said light-receiving means through the reflection of the reflecting surface, in which said shield means comprises a concave mirror, the focus of said concave mirror being disposed at said light-receiving means, and in which said irradiating means is directed toward the reflection surface of the object, said shield means being disposed in opposed relation to said irradiating means in such a manner that the illuminating light is fed to said shield means through the reflection by the reflection surface of the object.

2. Apparatus according to claim 1, further comprising an elongated body, said irradiating means and said light-receiving means being mounted on one end of said body.

3. An apparatus according to claim 1, further comprising an elongated body, an image-transmitting optical system being mounted in said elongated body and including a bundle of optical fibers extending along said elongated body, said bundle of optical fibers having one end thereof disposed at one end of said elongated body to form said irradiating means.

4. An apparatus according to claim 3, wherein said light-receiving means is disposed at said one end of said elongated body, and said image-transmitting optical system has an optical axis extending substantially parallel to an axis of said bundle of optical fibers.

* * * * *